(12) United States Patent
Anderson et al.

(10) Patent No.: US 9,227,036 B2
(45) Date of Patent: Jan. 5, 2016

(54) IRRIGATION CATHETER AND A METHOD OF FABRICATING

(75) Inventors: Neil Lawrence Anderson, Roseville (AU); Evan Ka-Loke Chong, South Strathfield (AU); James Panos, Kingsford (AU); Zoran Milijasevic, Bayview (AU)

(73) Assignee: CathRX LTD, Homebush Bay (AU)

( * ) Notice: Subject to any disclaimer, the term of this patent is extended or adjusted under 35 U.S.C. 154(b) by 1240 days.

(21) Appl. No.: 13/132,289

(22) PCT Filed: Dec. 4, 2009

(86) PCT No.: PCT/AU2009/001583
§ 371 (c)(1),
(2), (4) Date: Jun. 1, 2011

(87) PCT Pub. No.: WO2010/063078
PCT Pub. Date: Jun. 10, 2010

(65) Prior Publication Data
US 2012/0029444 A1 Feb. 2, 2012

Related U.S. Application Data

(60) Provisional application No. 61/200,988, filed on Dec. 5, 2008.

(51) Int. Cl.
*A61M 25/00* (2006.01)
*A61B 19/00* (2006.01)
(Continued)

(52) U.S. Cl.
CPC ............ *A61M 25/0012* (2013.01); *A61B 19/54* (2013.01); *A61B 2017/00526* (2013.01); *A61B 2018/00011* (2013.01); *A61B 2217/007* (2013.01); *A61M 25/005* (2013.01)

(58) Field of Classification Search
CPC .................. A61B 18/1492; A61B 2018/1472; A61B 2018/00577; A61B 2018/0016; A61B 2018/1435; A61B 2218/002; A61M 25/0045; A61M 25/0012

USPC ...................................................... 604/20, 21
See application file for complete search history.

(56) References Cited

U.S. PATENT DOCUMENTS 5,782,811 A * 7/1998 Samson et al. ................ 604/527
6,010,500 A * 1/2000 Sherman et al. ................ 606/41
(Continued)

FOREIGN PATENT DOCUMENTS

JP 2002143322 A 5/2002
JP 2008220959 A 9/2008
(Continued)

OTHER PUBLICATIONS

Supplemental European Search Report for corresponding application No. EP 09 82 9893, issued Mar. 15, 2012, 6 pages.
(Continued)

*Primary Examiner* — Bhisma Mehta
*Assistant Examiner* — Bradley Osinski
(74) *Attorney, Agent, or Firm* — TraskBritt

(57) ABSTRACT

A catheter sheath for an irrigation catheter comprises an elongate member having a proximal end and a distal end and defining a lumen extending from the proximal end to the distal end. At least one electrode is arranged on the elongate member. A plurality of elongate elements are contained in the elongate member, the elongate elements comprising at least one electrical conductor and at least one element of a non-conductive material arranged adjacent the at least one electrical conductor to form at least one non-conductive region associated with the elongate member. At least one passage extends through a wall of the elongate member to intersect the non-conductive region and to be in communication with the lumen of the elongate member. The at least one passage has an outlet opening in, or adjacent, the at least one electrode.

24 Claims, 5 Drawing Sheets

(51) Int. Cl.
*A61B 18/00* (2006.01)
*A61B 17/00* (2006.01)

(56) References Cited

U.S. PATENT DOCUMENTS

| | | | |
|---|---|---|---|
| 6,607,502 B1 * | 8/2003 | Maguire et al. | 604/22 |
| 6,978,185 B2 * | 12/2005 | Osypka | 607/122 |
| 2004/0220549 A1 * | 11/2004 | Dittman et al. | 604/526 |
| 2006/0287650 A1 | 12/2006 | Cao et al. | |
| 2008/0249522 A1 | 10/2008 | Pappone et al. | |

FOREIGN PATENT DOCUMENTS

| | | |
|---|---|---|
| WO | WO9618339 | 6/1996 |
| WO | WO0062851 | 10/2000 |
| WO | 0105210 A2 | 1/2001 |
| WO | 0232497 A1 | 4/2002 |
| WO | WO0232497 | 4/2002 |
| WO | WO2004091710 | 10/2004 |
| WO | 2005048858 A1 | 6/2005 |
| WO | 2005112814 A2 | 12/2005 |
| WO | WO0001313 | 4/2011 |

OTHER PUBLICATIONS

Japanese Search Report for corresponding application No. P2011-538799, dated Oct. 9, 2013, 3 pages.
International Search Report and Written Opinion for PCT/AU2009/001583, dated Feb. 15, 2010.
International Preliminary Report on Patentability, for International Application No. PCT/AU2009/001583, dated Jun. 7, 2011, 13 pages.

* cited by examiner

IRRIGATION CATHETER AND A METHOD OF FABRICATING

CROSS-REFERENCE TO RELATED APPLICATIONS

This is a national phase entry under 35 U.S.C. §371 of International Patent Application PCT/AU2009/001583, filed Dec. 4, 2009, published in English as International Patent Publication WO 2010/063078 A1 on Jun. 10, 2010, which claims the benefit of U.S. Provisional Patent Application Ser. No. 61/200,988, filed on Dec. 5, 2008, the entire disclosure of each of which is hereby incorporated herein by this reference.

TECHNICAL FIELD

This disclosure relates, generally, to catheters and, more particularly, to a method of fabricating a catheter sheath for an irrigation catheter and to a catheter sheath made in accordance with the method.

BACKGROUND

In the heat treatment of a biological site in a patient's body, it is often necessary to cool the site being treated to inhibit damage to tissue at the site in the patient's body. Cooling is generally effected by irrigating the site with an appropriately sterilized liquid. The liquid is conveyed to an outlet opening through a conduit in a catheter.

The Applicant has filed an International Patent Application for an electrical lead under International Patent Application Number PCT/AU01/01339 dated Oct. 19, 2001. The electrical lead forming the subject matter of the International Patent Application has an unimpeded lumen and is suitable as a catheter sheath of an irrigation catheter. It lends itself to this application due to the fact that the unimpeded lumen facilitates insertion of items to assist in maneuvering and manipulating the electrode sheath while retaining a narrow diameter sheath which is beneficial in steering the catheter through the vascular system of the patient to the site of interest. The lumen can also be used as the conduit for the passage of the irrigation fluid to be emitted at a distal region while still maintaining the benefit of a catheter sheath having a narrower diameter than other catheters of which the Applicant is aware.

Throughout this specification the word "comprise," or variations such as "comprises" or "comprising," will be understood to imply the inclusion of a stated element, integer or step, or group of elements, integers or steps, but not the exclusion of any other element, integer or step, or group of elements, integers or steps.

DISCLOSURE

In a first aspect, there is provided a method of fabricating a catheter sheath for an irrigation catheter, the method comprising:

providing a tubular member defining a lumen;
arranging a plurality of elongate elements about the tubular member, the elongate elements comprising at least one electrical conductor and at least one length of a non-conductive element arranged adjacent the at least one electrical conductor to form at least one non-conductive region on the tubular member;
applying an outer layer to the elongate elements to cover the elongate elements; and
forming at least one passage extending from the outer layer, through the non-conductive region and the tubular member, to be in communication with the lumen of the tubular member.

The method may include arranging the at least one electrical conductor and the at least one non-conductive element helically about the tubular member to form a helically extending non-conductive region about the tubular member. Preferably, the method includes arranging a plurality of conductors helically about the tubular member, the conductors being arranged in groups and the at least one non-conductive element being interposed between two of the groups. Preferably, a plurality of non-conductive elements arranged side-by-side are interposed between the at least two groups. Optionally, each group of conductors may have a set of non-conductive elements associated with it.

The method may include, after the outer layer has been applied, accessing a portion of the at least one electrical conductor and removing insulation from the at least one electrical conductor. Preferably, the at least one electrical conductor is accessed by removing a portion of the outer layer, for example, by laser cutting the outer layer. The laser may also be used to remove the insulation from the at least one electrical conductor.

The method may include applying an electrically conductive adhesive to the portion of the at least one electrical conductor that has been accessed. The electrically conductive adhesive may comprise a silver filled epoxy. At least some of the silver particles of the silver filled epoxy may be coated with platinum or palladium.

The method may include applying at least one layer of electrically conductive material to the electrically conductive adhesive to form an electrode on a surface of the outer layer. Instead, or in addition, the method may include overlaying the electrically conductive adhesive with a bio-compatible metal element, such as a metal ring containing platinum, to form an electrode on the outer layer.

The method may include forming the at least one passage through, or adjacent, the electrode formed on the outer layer.

The method may include arranging a radio opaque marker beneath the electrode to provide radio-opacity at the location of the electrode. The method may include arranging the radio opaque marker about the periphery of the tubular member prior to arranging the plurality of elongate elements about the tubular member so that the elongate elements overlie the at least one radio opaque marker.

The method may include forming the at least one radio opaque marker by winding a filamentary element about the tubular member. The method preferably includes winding the elongate element in an opposite sense to at least one pair of conductors.

Further, the method may include, in the region of the electrode, winding the filamentary element with a closer pitch than in other regions of the elongate member.

The method may include interposing a sleeve between the tubular member and the outer layer at least to partially cover the winding.

The method may include accessing a portion of each of different electrical conductors at longitudinally spaced intervals along the outer layer and forming an electrode in association with each electrical conductor accessed, the electrodes being arranged at longitudinally spaced intervals along the outer layer. Then, the method may include forming at least one passage in association with each of at least some of the electrodes. It will be appreciated that, where the radio opaque winding is provided, a radio opaque marker may be associated with at least some and, preferably, all of the electrodes.

The method may include varying a cross-sectional dimension of the passages to effect a substantially uniform flow rate of fluid through the passages. By "uniform flow rate" is meant that the volume of fluid through each passage per unit of time is substantially the same. Preferably, the method includes varying the cross-sectional dimension of the passages by progressively increasing the cross-sectional dimension from a proximal passage to a distal passage.

The method may include sealing a wall of the at least one passage against the ingress of detritus. The sealing of the wall of the at least one passage may be effected by applying a wicking adhesive to the wall of the at least one passage.

In a second aspect, there is provided a method of fabricating a catheter sheath for an irrigation catheter, the method comprising:
- providing an elongate member having a tubular member defining a lumen, a plurality of elongate elements arranged about the tubular member, the elongate elements comprising at least one electrical conductor and at least one element of a non-conductive material arranged adjacent the at least one electrical conductor to form at least one non-conductive region about the elongate member and an outer layer applied to the elongate elements to cover the elongate elements; and
- forming at least one passage through a wall of the elongate member, passing through the at least one non-conductive region, to be in communication with the lumen of the elongate member.

The method may include helically arranging the elongate elements about the tubular member.

The catheter sheath may include at least one electrode on a surface of the outer layer, the at least one electrode being in electrical communication with the at least one electrical conductor and the method may include forming the at least one passage through, or adjacent, the at least one electrode.

In a third aspect, there is provided a catheter sheath for an irrigation catheter, the catheter sheath comprising:
- an elongate member having a proximal end and a distal end and defining a lumen extending from the proximal end to the distal end;
- a plurality of elongate elements contained in the elongate member, the elongate elements comprising at least one electrical conductor and at least one element of a non-conductive material arranged adjacent the at least one electrical conductor to form at least one non-conductive region associated with the elongate member; and
- at least one passage extending through a wall of the elongate member to intersect the non-conductive region and to be in communication with the lumen of the elongate member.

The elongate elements may be contained in the wall of the elongate member. Preferably, the elongate elements are helically arranged in the wall of the elongate member to define at least one helical non-conductive region in the wall of the tubular member.

The catheter sheath may include a plurality of electrical conductors, the conductors being arranged in groups and the at least one non-conductive element being arranged between two of the groups. Preferably, the groups of conductors are separated by a plurality of elements of non-conductive material arranged side-by-side.

The elongate member may comprise an inner tubular member about which the elongate elements are arranged and an outer layer which covers the elongate elements. In other words, the elongate elements are embedded in the wall of the tubular member being sandwiched between the inner tubular member and the outer layer.

Access may be gained to the at least one electrical conductor via an opening formed in the outer layer. The opening may contain an electrically conductive adhesive.

At least one layer of electrically conductive material may be applied to the electrically conductive adhesive to form an electrode on a surface of the outer layer. Instead, or in addition, the catheter sheath may include a metal element overlying the electrically conductive adhesive to form an electrode on the outer layer.

The at least one passage may be formed through, or adjacent, the electrode formed on the outer layer.

The catheter sheath may include a radio opaque marker underlying the electrode.

The radio opaque marker may be formed by a winding of a radio opaque material arranged about the tubular member, the winding providing radio-opacity at least the position of the electrode. Turns of the winding may have a closer pitch in the region of the electrode. The winding may be wound in an opposite sense to the at least one pair of conductors.

The winding may underlie the elongate elements. Further, the winding may be covered by a sleeve interposed between the tubular member and the outer layer.

The catheter sheath may include a plurality of electrodes arranged at longitudinally spaced intervals along the elongate member with a passage being associated with each of at least some of the electrodes. It will be appreciated that the winding may be wound to form a radio opaque marker associated with at least some and, preferably, all of the electrodes.

A cross-sectional dimension of the passages may vary to effect a substantially uniform flow rate of fluid through the passages. The cross-sectional dimension of the passages may vary by being progressively larger from a proximal passage to a distal passage.

A wall of the at least one passage may be sealed against the ingress of detritus.

In a fourth aspect, there is provided a catheter sheath for an irrigation catheter, the catheter sheath comprising:
- an elongate member having a proximal end and a distal end and defining a lumen extending from the proximal end to the distal end;
- a plurality of electrical conductors contained in the elongate member; and
- a plurality of electrodes arranged at longitudinally spaced intervals along the elongate member with each electrode being in electrical communication with at least one associated electrical conductor through the elongate member and there being a passage associated with each of at least some of the electrodes, each passage extending from an outer surface of the elongate member to be in communication with the lumen of the elongate member and a cross-sectional dimension of the passages varying to effect a substantially uniform flow rate of fluid through the passages.

The cross-sectional dimension of the passages may vary by being progressively larger from a proximal passage to a distal passage.

DETAILED DESCRIPTION OF THE INVENTION

Figure 1:
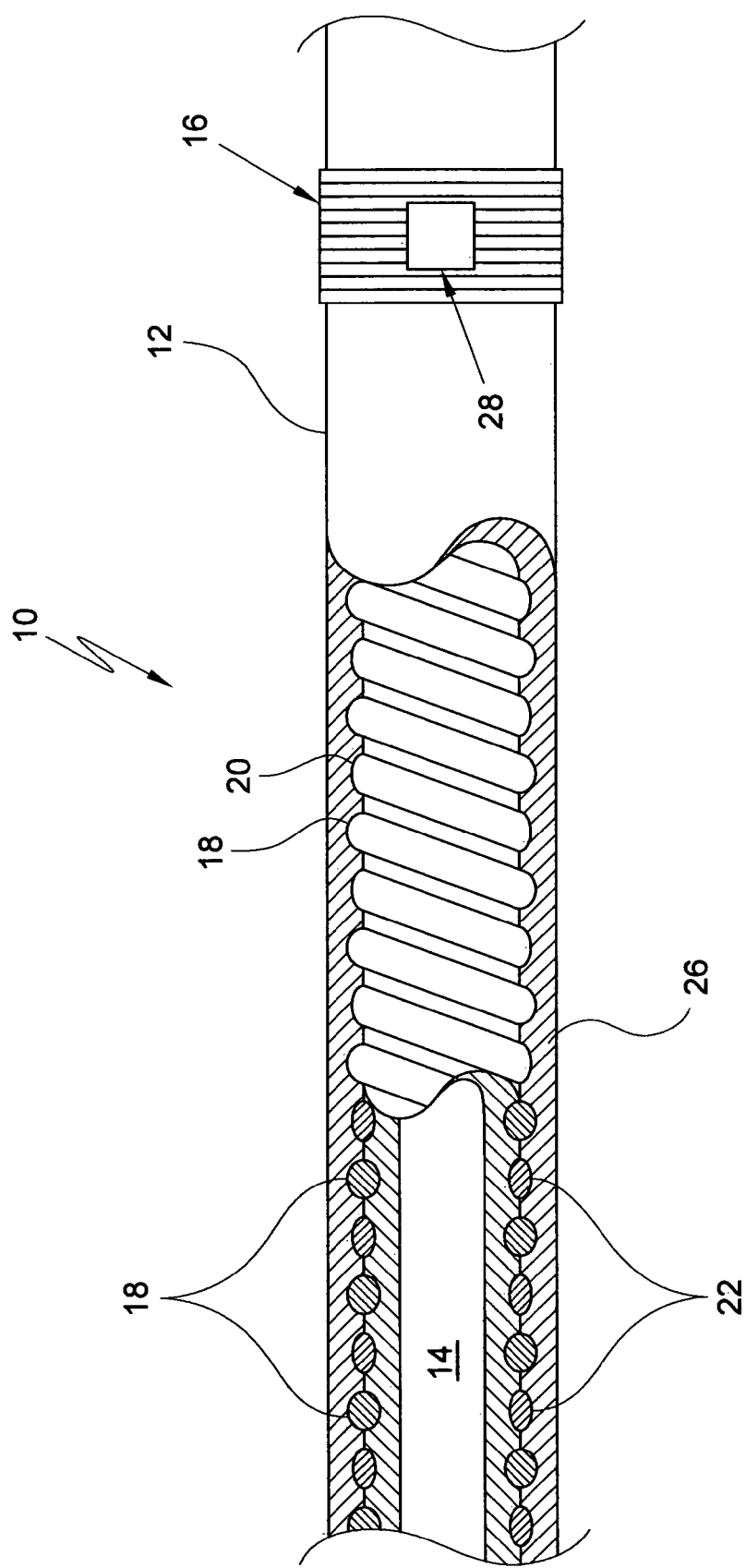
FIG. 1 shows, schematically, a partially sectioned side view of an embodiment of a catheter sheath.

In the drawings, reference numeral 10 generally designates an embodiment of a catheter sheath. The sheath 10 comprises an elongate member 12 having a proximal end and a distal end and defining a lumen 14 extending from the proximal end to the distal end. At least one electrode 16 is arranged on the elongate member 12.

While reference has been made to only one electrode 16, it will be appreciated that, generally, the catheter sheath 10 has a plurality of axially spaced electrodes 16. Thus, the catheter sheath 10 could carry up to twenty electrodes 16 in longitudinally spaced intervals. Further, although the electrodes 16 will more often than not be annular, they could be other shapes such as pads, cuffs (extending only partway about the periphery of the elongate member 12), or the like.

A plurality of elongate elements 18, 20 are contained in the elongate member 12, the elongate elements comprising at least one electrical conductor 18 associated with each electrode 16 and at least one element 20 of a non-conductive material arranged adjacent the conductors 18 to form at least one non-conductive region 22 associated with the elongate member 12. At least one passage 24 (FIG. 3) extends through a wall 26 of the elongate member 12 to intersect the non-conductive region 22 and to be in communication with the lumen 14 of the elongate member 12. The passage 24 has an outlet opening 28 in, or adjacent, its associated electrode 16.

While only a single electrical conductor 18 has been shown, each electrode 16 may have up to four conductors 18 associated with it. Thus, a pair of conductors 18 is used for transmission of detected signals at a site in a patient's body where the electrode 16 is located and/or for the transmission of ablation energy, such as radio frequency (RF) energy, to the site. A copper wire/Constantin pair is used as a thermocouple for temperature measuring purposes.

Further, while only one element 20 of a non-conductive material has been illustrated, it is preferred that a plurality of such elements 20 be arranged side-by-side to form a non-conductive region 22 of sufficient width to be intersected by the passage 24. For example, four or five such elements 20 could be arranged in abutting side-by-side relationship. As will be described with reference to FIGS. 2a-2f below, the conductors 18 and the elements 20 are wound helically in the wall 26 of the elongate member 12 and the elements 20 abut the conductors 18.

The non-conductive elements 20 are of any suitable material such as, for example, polyester fibers. Each electrode 16 requiring irrigation may have a set of elements 20 associated with it. Instead, only one set of elements 20 may be provided to be accessed at the desired position along the length of the elongate member 12.

Figure 2A:
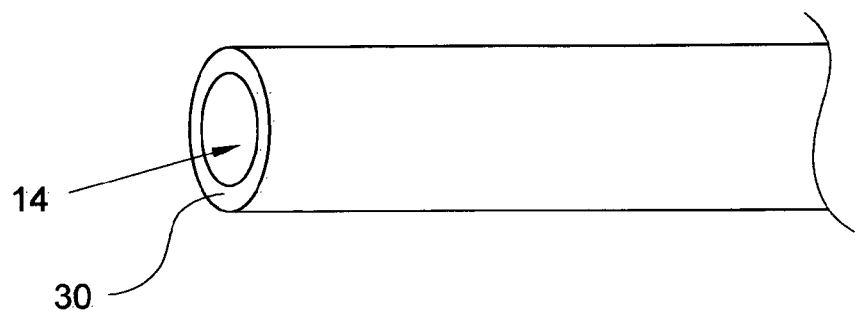
FIGS. 2a-2f show, schematically, steps of an embodiment of a method for fabricating the catheter sheath of FIG. 1.

With reference to FIGS. 2a-2f, an embodiment of a method of fabricating an irrigation catheter is described in greater detail. Initially, as shown in FIG. 2a, an inner, tubular member 30 is provided. The tubular member 30 is made from a suitable polymeric material such as polyethylene or polyether block amide (PEBAX®). Other suitable, bio-compatible polymeric materials could also be used.

Figure 2B:
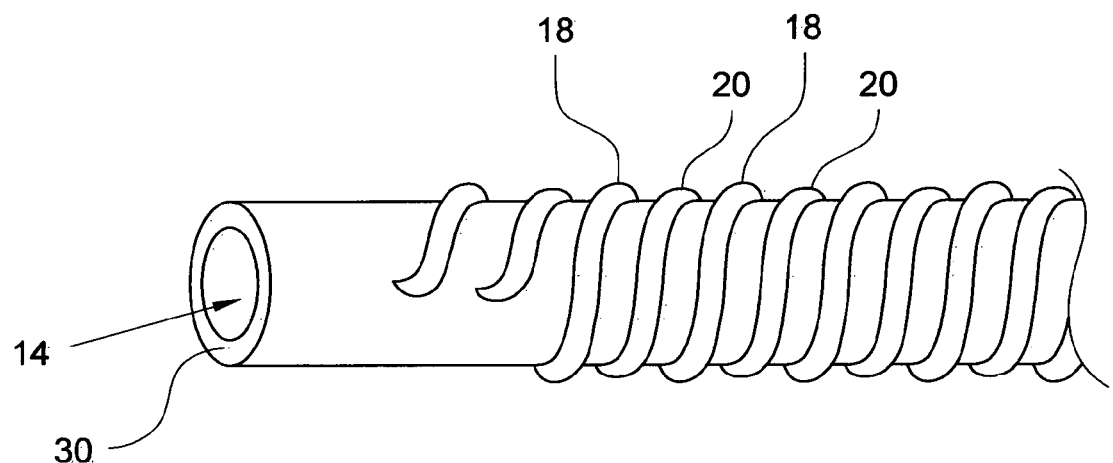

Initially, a plurality of conductors 18 and non-conductive elements 20 are helically wound about an outer surface of the tubular member 30 as shown in FIG. 2b. While a single conductor 18 and a single elongate element 20 are shown in FIG. 2b, as described above, there are normally a plurality of conductors 18 arranged side-by-side with at least one set, preferably about four or five elements, of non-conductive elements 20. Further, while FIG. 2b illustrates the conductors 18 and elements 20 as being spaced from each other, this is purely for illustrative purposes. In practice, the conductors 18 and the non-conductive elements 20 are arranged side-by-side in a substantially abutting relationship.

In other embodiments of the invention, the conductors 18 and elongate elements 20 may extend axially along the outer surface of the tubular member 30 or, instead, may be contained within the lumen 14 of the tubular member 30.

Figure 2C:
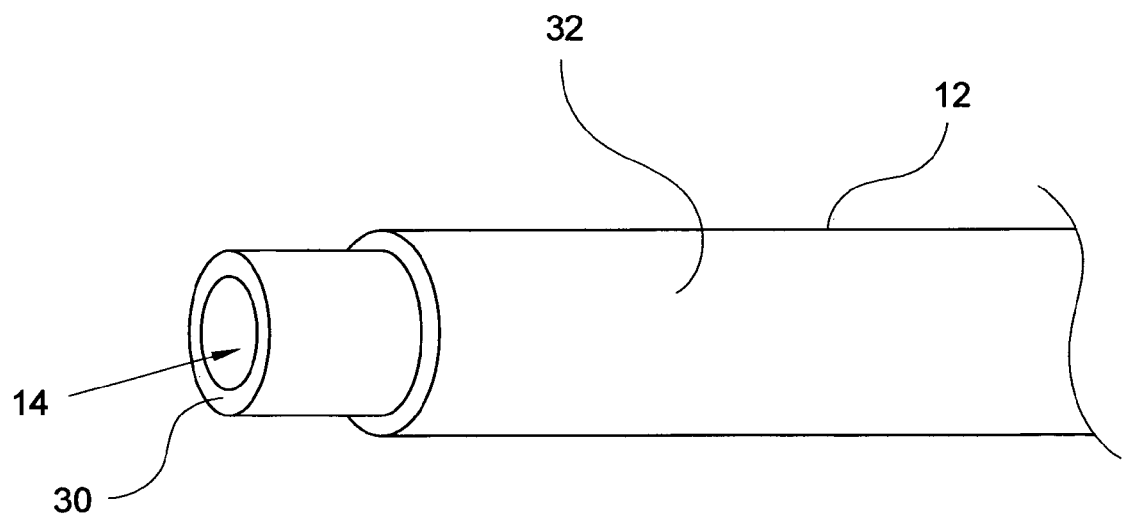

An outer layer 32 is applied over the elongate elements 18, 20 as shown in FIG. 2c of the drawings. The outer layer 32 is applied in various ways. For example, the outer layer 32 can be applied as a jacket which is extruded over the elongate elements 18, 20, applied as a liquid which is allowed to set, or the like. Once the outer layer 32 has been applied, the elongate member 12 is complete.

The outer layer 32 is formed of a similar material to the tubular member 30 but is, preferably, of a light-transparent material so that the elongate elements 18, 20 can be seen through the outer layer 32 to enable the conductors 18 and the elements 20 to be accessed.

When the outer layer 32 is applied as an extrusion in the form of a jacket, the elongate member 12 comprising the inner member 30, the elongate elements 18, 20 and the outer layer 32 are heat treated to secure the outer layer 32 to the tubular member 30 and to the elongate elements 18, 20. In so doing, the elongate elements 18, 20 are effectively sandwiched between the inner, tubular member 30 and the outer layer 32 to be embedded in the wall 26 (FIG. 1) of the elongate member 12. Because there is very little, if any, polymeric material between the elongate elements 18, 20 the flexibility of the elongate member 12 is improved.

Figure 2D:
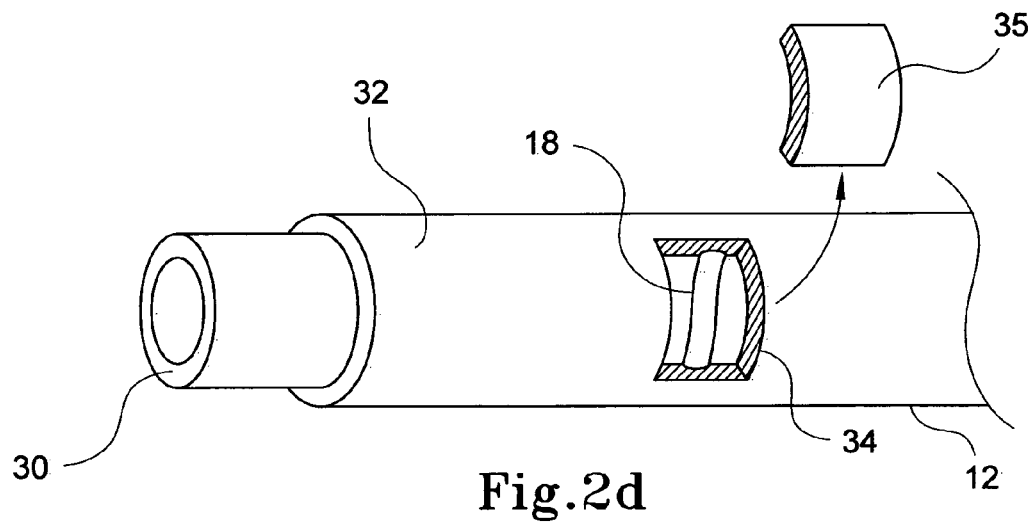
Figure 2E:
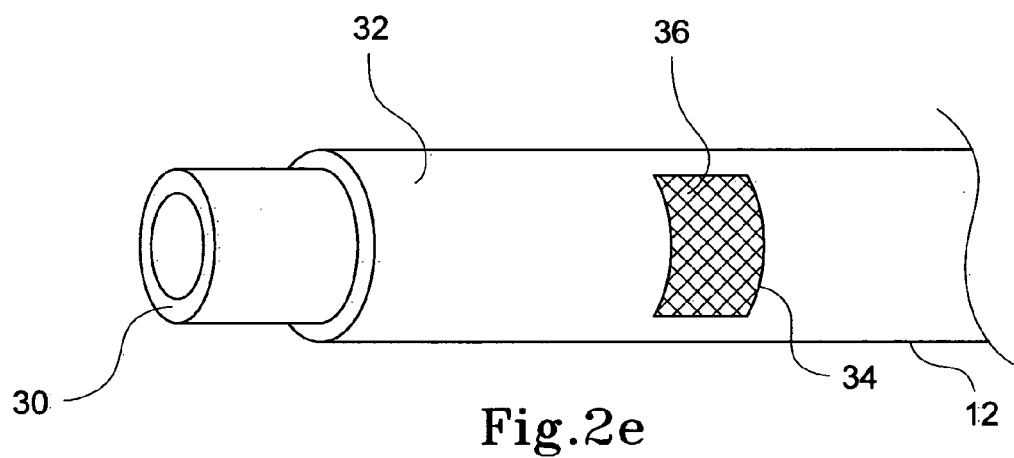

To form each electrode 16 on the elongate member 12, the desired conductors 18 are accessed by forming an opening 34 in the outer layer 32 as shown in FIG. 2d of the drawings. A portion 35 of the outer layer 32 is removed, for example, by laser cutting. Laser cutting facilitates accurate cutting of the outer layer 32 and only those conductors 18 desired to be accessed over a desired length are revealed by removing the portion 35 of the outer layer 32. The insulation of each conductor 18 which has been accessed is also removed by laser cutting at the time that the portion 35 is removed from the outer layer 32 by the laser cutting operation.

After removal of the portion 35 of the outer layer 32 of the elongate member 12, the exposed conductors 18 are covered with an electrically conductive adhesive 36 which is charged into the opening 34 substantially to fill the opening 34.

The electrically conductive adhesive 36 is a silver-filled epoxy. If desired, at least some of the silver particles of the silver-filled epoxy are coated with platinum or palladium.

Figure 2F:
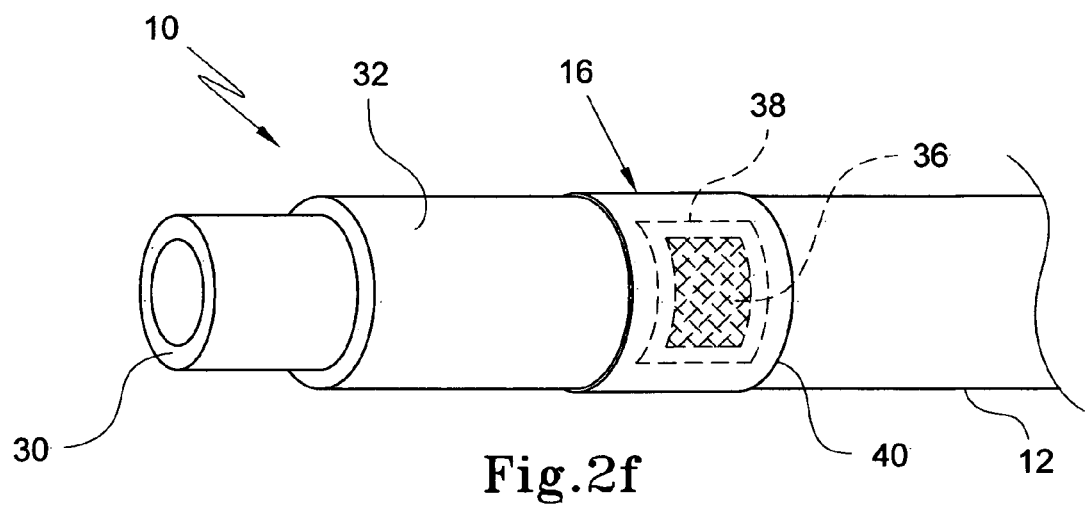

As shown in FIG. 2f of the drawings, the method further comprises the step of covering the electrically conductive adhesive 36 with a further layer 38 of an electrically conductive material. The electrically conductive material may be any of a variety of materials but particularly suitable materials are those which are able to form a conductive layer between the electrically conductive adhesive 36 and any additional material placed externally to the layer 38. Appropriate classes of such electrically conductive materials are liquid carriers, particularly volatile carriers such as solvents, variously containing solvated or complexed conductors or containing solid conductors. The sub-class of these materials may be inks containing particulate conductive metals, alloys or constructs such as silver or silver coated with metal such as platinum or palladium.

The layer 38 may be applied in one of a variety of ways, for example, by spraying, by electrostatic deposition, by direct application as by brush, pad, or the like. The Applicant has found that good results are obtained using pad printing with silver filled ink, palladium filled ink or a palladium/solvent ink combination.

A further step of catalyzing the layer 38 involves the use of an acidic palladium chloride solution to deposit a coating of palladium on the silver of the layer 38.

Once the layer 38 has been formed over the adhesive 36, the layer 38 can be used as an electrode. Such an electrode can be used for sensing purposes. However, and, preferably, the layer 38 is overlaid with a layer 40 of bio-compatible material, such as platinum, to increase electrical conductivity across the electrode 16. Preferably, the layer 40 extends about the circumference of the outer layer 32 of the elongate member 12 to form a ring electrode. The layer 40 is deposited by electroless plating but could also be applied by other metal deposition techniques. Further, the layer 40 need not extend completely about the circumference but could be cuff shaped to form an electrode extending partway about the circumference of the outer layer 32.

In another embodiment, not shown, a ring is applied over the layer 38 and is secured in position by appropriate techniques such as, for example, crimping, adhesive or other securing techniques to form the final electrode 16 of the catheter sheath 10.

Figure 3:
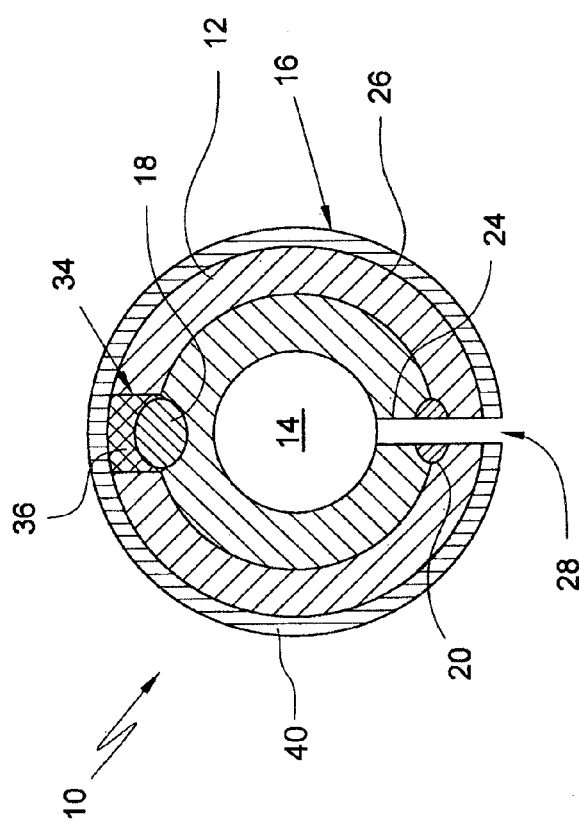
FIG. 3 shows, schematically, on an enlarged scale, a cross-sectional view of the catheter sheath of FIG. 1 after completion of the method of FIGS. 2a-2f.

Finally, the opening 28 is formed in the layer 40 as shown in FIG. 3 of the drawings and the passage 24 is formed to intersect the non-conductive region 22 (FIG. 1) and to access the lumen 14 of the elongate member 12. Thus, a passage 24 for irrigation fluid through the electrode 16 is provided. It will be appreciated that more than one such passage 24 may be provided for each electrode 16, for example, being spaced approximately 90° from each other. Further, while the passage 24 is shown in FIG. 3 as being spaced 180° from the opening 34 accessing the conductor 18, it will be appreciated that this is for illustrative purposes only. The opening 28 and the associated passage 24 can be positioned anywhere about the periphery of the electrode 16. Further, the passage 24 may not extend through the electrode 16 but could, rather, be arranged in the elongate member 12 adjacent the electrode 16.

After the formation of each passage 24, a wall of the passage 24 is sealed to inhibit the ingress of detritus such as blood or other fluids into the elongate member 12. The wall of the passage 24 is, preferably, sealed using a wicking adhesive. Suitable adhesives are low viscosity epoxies, such as Epo-Tec 301 from Epoxy Technology, or cyanoacrylates, such as LOCTITE® Cyanoacrylate 4014.

Figure 4:
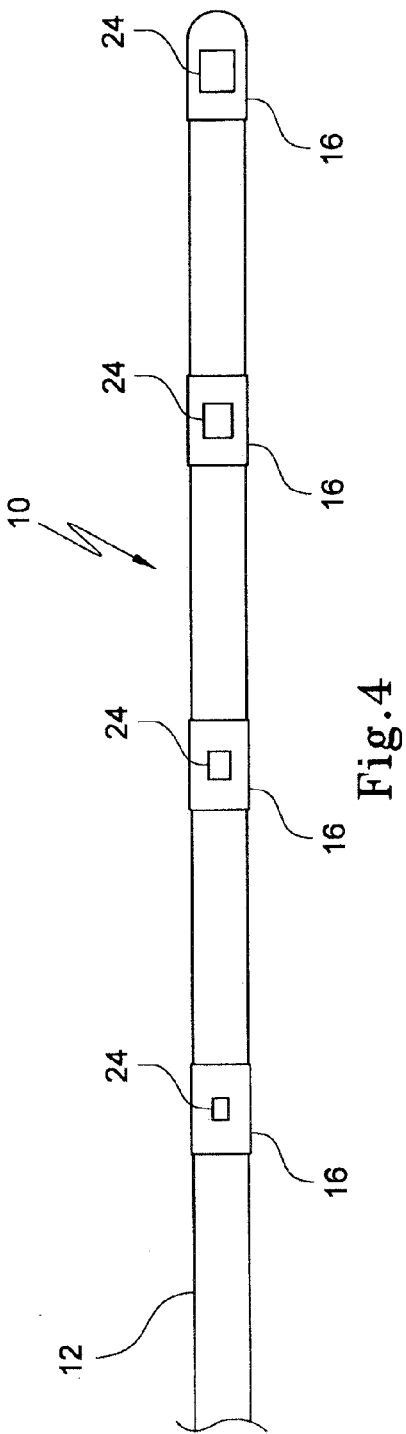
FIG. 4 shows a side view of a distal part of the catheter sheath.

In FIG. 4 a distal part of an embodiment of a catheter sheath 10 is illustrated. With reference to the previous drawings, like reference numerals refer to like parts unless specified. In this embodiment, a cross-sectional dimension of the passages 24 associated with the electrodes 16 varies to achieve a substantially uniform flow rate of irrigation fluid through the passages 24, in use. More particularly, the cross-sectional dimension of the passages 24 increases progressively from a proximal electrode 16 to a distal electrode 16. In the case of a square or rectangular passage 24, the cross-sectional dimension is the diagonal of the passage 24 whereas, in the case of a circular passage 24, the cross-sectional dimension is the diameter of the passage 24.

Figure 5:
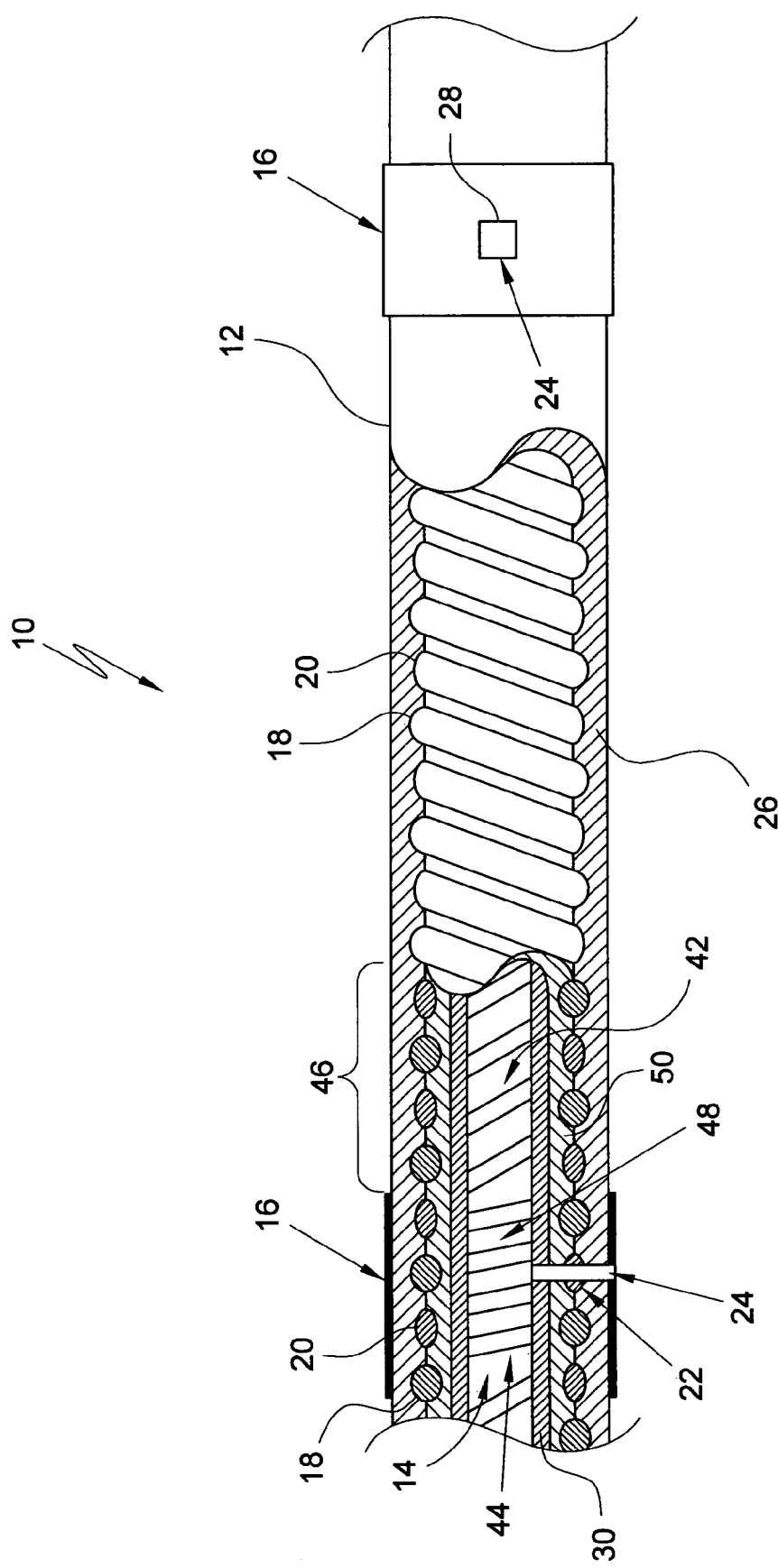
FIG. 5 shows, schematically, a partially sectioned side view of a further embodiment of a catheter sheath.

Referring to FIG. 5 of the drawings, a part of a further embodiment of a catheter sheath is illustrated. Once again, with reference to the previous drawings, like reference numerals refer to like parts unless otherwise specified.

In this embodiment, a radio-opaque marker 42 is associated with each of at least some of the electrodes 16. Preferably, each electrode 16 has a radio-opaque marker 42 associated with it. The radio opaque markers 42 are formed by a winding 44 of a bio-compatible radio-opaque material such as, for example, tantalum, platinum, tungsten, or the like. The winding 44 is arranged about the tubular member 30 with varying pitch of turns of the winding 44 so that, beneath each electrode 16, the winding 44 is close pitched, i.e., with turns of the winding 44 closer together, and, between the electrodes 16, the turns of the winding 44 have a greater pitch as shown at 46 in FIG. 5 of the drawings.

In this embodiment, the close pitched turns still have a spacing between them as shown at 48 so that the passage 24 can pass between adjacent turns without intersecting any one of the turns.

In the fabrication of this embodiment of the catheter sheath 10, after the winding 44 has been applied to the tubular member 30, a sleeve 50 of a plastics material is applied over the winding 44 to insulate the winding from the subsequently applied conductors 18. The sleeve 50 could be applied by coating molten plastics material over the winding 44 and allowing it to set or the sleeve 50 could be applied as an extrusion which is heat shrunk in position over the winding 44.

The sleeve 50 provides a smoother constant cross-section for the elongate member 12 and serves to inhibit cross-connection between the winding 44 and the conductors 18. The sleeve 50 is of a similar material to the tubular member 30 such as PEBAX®, but is of a softer grade than that of the tubular member 30 as well as the outer layer 32 to maintain the flexibility of the elongate member 12.

Preferably, the winding 44 and the elongate elements 18, 20 are wound in opposite senses. With this arrangement, the flexibility of the catheter sheath 10 is maintained while enhancing kink resistance of the catheter sheath 10. It is noted that in this embodiment too, the conductors 18 and the non-conductive elements 20 are shown as being spaced from each other but this is purely for the sake of explanation. In practice, the conductors 18 and the non-conductive elements 20 are arranged helically in abutting relationship.

It is an advantage of the described embodiments that the Applicant's manufacturing technique for a catheter sheath lends itself to the use of non-conductive elongate elements to be positioned within the wall of the elongate member 12. Thus, an irrigation passage 24 can be formed in a cost-effective way. Advantageously, an irrigation catheter is able to be provided which is of substantially smaller diameter than other catheter sheaths of which the Applicant is aware. Due to the manufacturing technique employed, the catheter sheath need be no wider than a conventional non-irrigation catheter. This is beneficial for the ease with which a clinician can steer the catheter through a patient's vasculature and which inhibits the likelihood of trauma being caused to the patient's vasculature as the catheter is steered through the patient's body.

It will be appreciated by persons skilled in the art that numerous variations and/or modifications may be made to the catheter sheath and associated method as shown in the specific embodiments without departing from the broadly described scope. The present embodiments are, therefore, to be considered in all respects as illustrative and not restrictive.

The invention claimed is:

1. A catheter sheath for an irrigation catheter, the catheter sheath comprising:

an elongate member having a proximal end and a distal end and defining a lumen extending from the proximal end to the distal end;

a plurality of elongate elements helically embedded in the elongate member, the plurality of elongate elements comprising at least one electrical conductor and at least one element of a non-conductive material arranged adjacent the at least one electrical conductor to form at least one non-conductive region associated with the elongate member; and at least one passage extending through a wall of the elongate member to intersect the non-conductive region and to be in communication with the lumen of the elongate member.

2. The catheter sheath of claim 1, wherein the plurality of elongate elements are attached to the wall of the elongate member.

3. The catheter sheath of claim 2, wherein the plurality of elongate elements are helically arranged in the wall of the elongate member to define at least one helical non-conductive region in the wall of the elongate member.

4. The catheter sheath of claim 1, wherein the at least one electrical conductor includes a plurality of electrical conductors, the plurality of electrical conductors being arranged in groups and the at least one element of a non-conductive material being arranged between two of the groups.

5. The catheter sheath of claim 4, wherein the at least one element of a non-conductive material comprises a plurality of elements of non-conductive material arranged side-by-side, and the groups of electrical conductors are separated by the plurality of elements of non-conductive material arranged side-by-side.

6. The catheter sheath of claim 1, wherein the elongate member comprises an inner tubular member about which the plurality of elongate elements is embedded and an outer layer that covers the elongate elements.

7. The catheter sheath of claim 6, wherein access is gained to the at least one electrical conductor via an opening formed in the outer layer.

8. The catheter sheath of claim 7, wherein the opening contains an electrically conductive adhesive.

9. The catheter sheath of claim 8, further comprising an electrode on a surface of the outer layer over the electrically conductive adhesive.

10. The catheter sheath of claim 9, wherein the electrode is formed by applying at least one layer of electrically conductive material to the electrically conductive adhesive.

11. The catheter sheath of claim 9, wherein the electrode is formed by applying a metal element overlying the electrically conductive adhesive.

12. The catheter sheath of claim 9, wherein the at least one passage is formed through, or adjacent, the electrode formed on the outer layer.

13. The catheter sheath of claim 9, further comprising a radio-opaque marker underlying the electrode.

14. The catheter sheath of claim 13, wherein the radio-opaque marker is formed by a winding of a radio-opaque material arranged about the inner tubular member, the winding providing radio-opacity at at least the position of the electrode.

15. The catheter sheath of claim 14, wherein turns of the winding have a closer pitch in the region of the electrode.

16. The catheter sheath of claim 14, wherein the winding underlies the plurality of elongate elements.

17. The catheter sheath of claim 14, wherein the winding is covered by a sleeve interposed between the inner tubular member and the outer layer.

18. The catheter sheath of claim 14, wherein the winding is helically arranged in an opposing direction to the helically arranged plurality of elongate elements.

19. The catheter sheath of claim 1, further comprising a plurality of electrodes arranged at longitudinally spaced intervals along the elongate member, wherein the at least one passage includes a plurality of passages, and at least some of the plurality of electrodes are associated with at least one of the plurality of passages.

20. The catheter sheath of claim 19, wherein a cross-sectional dimension of each of the plurality of passages varies to effect a substantially uniform flow rate of fluid through each of the plurality of passages.

21. The catheter sheath of claim 20, wherein the cross-sectional dimension of each of the plurality of passages varies by being progressively larger from a proximal passage to a distal passage of the plurality of passages.

22. The catheter sheath of claim 1, wherein a wall of the at least one passage is sealed against the ingress of detritus.

23. A catheter sheath for an irrigation catheter, the catheter sheath comprising:

an elongate member having a proximal end and a distal end and defining a lumen extending from the proximal end to the distal end;

a plurality of electrical conductors helically embedded in the elongate member;

at least one non-conductive member helically embedded within the elongate member and positioned adjacent at least one of the plurality of electrical conductors; and a plurality of electrodes arranged at longitudinally spaced intervals along the elongate member with each electrode of the plurality of electrodes being in electrical communication with at least one associated electrical conductor through the elongate member and there being a passage of a plurality of passages associated with at least some of the electrodes of the plurality of electrodes, each passage of the plurality of passages extending from an outer surface of the elongate member to be in communication with the lumen of the elongate member, wherein the at least one non-conductive member is intersected by at least one passage of the plurality of passages, and cross-sectional dimensions of the passages vary to effect a substantially uniform flow rate of fluid through the plurality of passages.

24. The catheter sheath of claim 23, wherein the cross-sectional dimensions of the plurality of passages vary by being progressively larger from a proximal passage of the plurality of passages to a distal passage of the plurality of passages.

* * * * *